United States Patent
Lee et al.

(10) Patent No.: US 11,857,716 B2
(45) Date of Patent: Jan. 2, 2024

(54) AUTOMATIC URINE TREATMENT SYSTEM

(71) Applicant: CRADERS Co., Ltd, Seoul (KR)

(72) Inventors: Ui Cheol Lee, Seoul (KR); Tae Hyun Kim, Gwangju-si (KR); Jung Hwan Kim, Seongnam-si (KR); Bo Ho Lee, Namyangju-si (KR)

(73) Assignee: CRADERS Co., Ltd, Seoul (KR)

( * ) Notice: Subject to any disclaimer, the term of this patent is extended or adjusted under 35 U.S.C. 154(b) by 314 days.

(21) Appl. No.: 17/146,962

(22) Filed: Jan. 12, 2021

(65) Prior Publication Data
US 2022/0193312 A1 Jun. 23, 2022

(30) Foreign Application Priority Data
Dec. 23, 2020 (KR) .................. 10-2020-0181545

(51) Int. Cl.
| | | |
|---|---|---|
| *A61M 1/00* | (2006.01) | |
| *A61F 5/44* | (2006.01) | |
| *G01N 21/78* | (2006.01) | |
| *G01N 33/493* | (2006.01) | |
| *A61F 5/451* | (2006.01) | |
| *A61F 5/441* | (2006.01) | |

(52) U.S. Cl.
CPC .............. *A61M 1/80* (2021.05); *A61F 5/441* (2013.01); *A61F 5/451* (2013.01); *G01N 21/78* (2013.01); *G01N 33/493* (2013.01)

(58) Field of Classification Search
CPC ........... A61M 1/80; A61F 5/441; A61F 5/451; G01N 21/78; G01N 33/493
USPC ........................................................ 604/319
See application file for complete search history.

(56) References Cited

U.S. PATENT DOCUMENTS

| | | | | |
|---|---|---|---|---|
| 3,402,243 | A * | 9/1968 | Gerow | .................. A61H 33/00 210/435 |
| 9,381,108 | B2 | 7/2016 | Longoni et al. | |
| 2011/0092786 | A1* | 4/2011 | Longoni | ................ A61B 5/201 600/345 |
| 2017/0020433 | A1* | 1/2017 | Hotaling | .............. A61B 10/007 |
| 2017/0119300 | A1* | 5/2017 | Conner | .............. G01F 23/2962 |

(Continued)

FOREIGN PATENT DOCUMENTS

| | | |
|---|---|---|
| JP | 0880318 A | 3/1996 |
| KR | 10-0831528 B1 | 5/2008 |
| KR | 20110104969 A | 9/2011 |

*Primary Examiner* — Andrew J Mensh
(74) *Attorney, Agent, or Firm* — NKL Law; Jae Youn Kim

(57) ABSTRACT

An automatic urine treatment system according to an embodiment of the present invention includes a receiver for receiving wearer's excrement; a main body including a urine tank for receiving and storing urine from the receiver, and a vacuum pump for sucking air into the urine tank and transferring a negative pressure to the receiver; and a first connecting hose connecting the receiver and the urine tank. A strip accommodation unit for accommodating a strip for analyzing components of the stored urine through color change is formed inside the urine tank, and on the outer surface of the urine tank, urine analysis is performed using a first optical sensor unit for sensing color change of the strip, and a second optical sensor unit for sensing at least one among turbidity and color change of the stored urine. There is an advantage of being able to confirm the health condition of disabled or elderly people in real-time through the urine information analyzed in this way.

9 Claims, 5 Drawing Sheets

(56) References Cited

U.S. PATENT DOCUMENTS

| | | | | |
|---|---|---|---|---|
| 2018/0202992 | A1* | 7/2018 | Speziale | G01N 35/1016 |
| 2020/0323700 | A1* | 10/2020 | Schiffer | A61B 5/6808 |
| 2020/0390423 | A1* | 12/2020 | Hall | G01N 35/1002 |

* cited by examiner

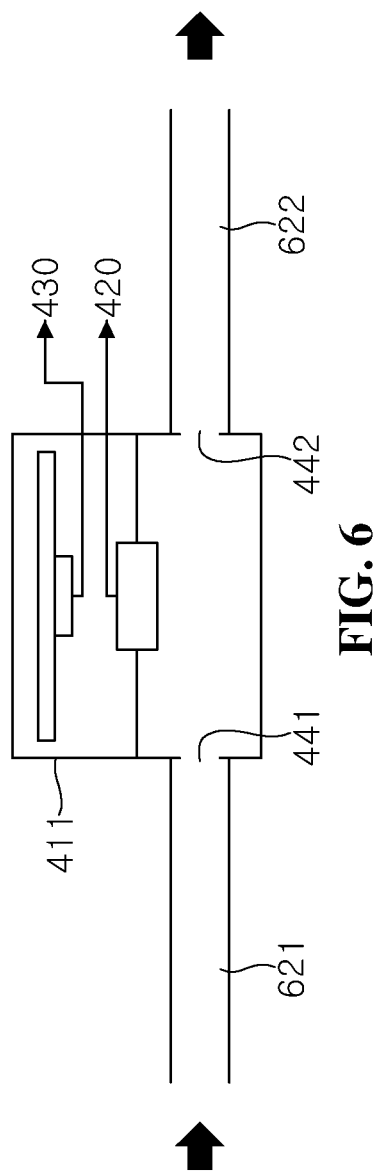

AUTOMATIC URINE TREATMENT SYSTEM

CROSS-REFERENCES TO RELATED APPLICATIONS

This application claims priority to and the benefit of Korean Patent Application No. 10-2020-0181545, filed on Dec. 23, 2020, the disclosure of which is incorporated herein by reference in its entirety.

BACKGROUND OF THE INVENTION

Field of the Invention

The present invention relates to an automatic urine treatment system that automatically performs urine treatment of an elderly person or a long-term care patient having a micturition disorder.

Background of the Related Art

The number of elderly people according to aging population and the number of people with acquired disabilities by traffic accidents or industrial accidents are increasing worldwide.

Among these people, patients with difficulties in excretion control among the long-term care patients who need long-term care cannot move or raise their bodies by themselves without help of healthcare assistants.

For these long-term care patients, a single healthcare assistant takes care of many patients, not usually at home. As excretion is not dealt with immediately at night or when the healthcare assistant is out of place, many problems such as bedsores, hygiene and the like are generated. In addition, the excretion treatment is the most difficult part for healthcare assistants, and it needs to resolve their fatigue.

In order to automatically process the excretion of long-term care patients, automatic excretion treatment devices are provided.

Conventional automatic excretion treatment devices are configured to absorb wearer's urine in a diaper-type receiver or a cup-type receiver and suck the urine absorbed in the receiver into a urine tank by applying a negative pressure.

These conventional automatic excretion treatment devices generate a negative pressure through a vacuum tank. The negative pressure generated in this way passes through the vacuum tank, the urine tank, and a connecting hose in order and is transferred to the receiver, and the urine is discharged from the receiver applied with the negative pressure, and stored in the urine tank through the connecting hose.

In the process of generating the negative pressure, the urine stored in the urine tank is discharged in the form of water vapor and transferred to the vacuum tank along a hose connecting the urine tank and the vacuum tank.

There is a problem in that as the water vapor transferred to the vacuum tank condenses inside the vacuum tank, it causes a failure of the vacuum tank.

In addition, although a negative pressure is applied to the receiver, a small amount of urine or wearer's sweat may not be transferred to the urine tank and generates skin trouble.

In addition, there is a problem in that although guardians are highly interested in whether healthcare of patients hospitalized in long-term care institutions is properly performed, it cannot be known.

In addition, there is a problem in that medical staff may not check health conditions of the hospitalized patients remotely.

SUMMARY OF THE INVENTION

An object of the present invention is to prevent corrosion of a vacuum pump by preventing transfer of moisture to the vacuum pump.

Another object of the present invention is to conduct health management by analyzing urine of an elderly or disabled person.

In addition, still another object of the present invention is to provide an automatic urine treatment system for preventing skin trouble of a wearer.

In addition, still another object of the present invention is to promote comfort of indoor air of a room equipped with an automatic urine treatment system.

To accomplish the above objects, according to one aspect of the present invention, there is provided an automatic urine treatment system including: a receiver for receiving wearer's excrement; a main body including a urine tank for receiving and storing urine from the receiver, and a vacuum pump for sucking air into the urine tank and transferring a negative pressure to the receiver; and a first connecting hose connecting the receiver and the urine tank.

A strip for analyzing components of the stored urine through color change may be mounted inside the urine tank.

The urine tank may further include a first optical sensor unit for sensing color change of the strip, and a second optical sensor unit for sensing at least one among turbidity and urine color of the stored urine.

The strip may include a plurality of color change units for analyzing components contained in the urine.

As the first optical sensor unit is installed in plurality at positions corresponding to the plurality of color change units, or light emitted from a single light source is split into as many lights corresponding to the color change units and transferred to each of the color change units, the first optical sensor units may detect color change of the plurality of color change units.

The automatic urine treatment system may further include: an auxiliary tank connected to the urine tank and the vacuum pump; a second connecting hose of which one end is connected to the urine tank and the other end is connected to an auxiliary tank; and a third connecting hose of which one end is connected to the auxiliary tank and the other end is connected to the vacuum pump.

The urine tank may include: a float sensor installed inside the urine tank to detect a level of the urine stored in the urine tank, and generate a urine level signal indicating the level of the stored urine; a mass sensor installed on an outer surface of the urine tank to detect a mass of the urine stored in the urine tank, and generate a urine mass signal indicating the mass of the stored urine; and an infrared sensor installed on the outer surface of the urine tank to detect foam of the urine, and generate a foam detection signal when the foam of the urine reaches a preset range.

A strip for analyzing urine components through color change may be mounted inside the urine tank.

The strip may include a strip support attached with a color change unit that changes color according to the urine components.

The strip support is mounted on a strip mounting unit, and the strip mounting unit may accommodate the strip support and be mounted on one side of the urine tank.

The strip mounting unit may include: a first support unit for supporting the strip support in a longitudinal direction; a second support unit perpendicular to the first support unit and supporting a first surface of the strip support; and a latch unit for supporting a second surface of the strip support and mounting the strip mounting unit on one side of the urine tank.

The latch unit may include a first bent unit and a second bent unit connected to the first bent unit.

The first bent unit may support a second surface of the strip support, and the second bent unit may be mounted on one side of the urine tank.

The receiver includes a first filter unit for filtering at least some of solid components from the excrement, and the first filter unit may include a first filter body having a mesh or pore structure of a water-permeable material.

At least one among grapefruit seed extract, kiwi fruit extract, camellia extract, chamomile extract, lavender extract, rosemary extract, coconut extract, olive extract, and zinc polypeptide may be contained in the first filter body.

The automatic urine treatment system may further include a second filter unit.

The second filter unit may be manufactured as a solid block by mixing and molding eucalyptus extract powder, lotus leaf extract powder, and a binder with activated carbon, or manufactured as a solid block by mixing and molding eucalyptus extract powder, lotus leaf extract powder, chlorine dioxide powder, and a binder with activated carbon.

A gas tank and a hole through which gas contained in excrement may pass may be formed on one side of at least one among the first connecting hose to the third connecting hose, and a gas sensor unit for sensing a gas component contained in the excrement may be formed on one side of at least one among the first connecting hose to the third connecting hose where the gas tank and the hole are formed.

The gas sensor unit may include a gas sensor for sensing a gas component of the excrement, a third filter for removing moisture of the gas, and an accommodation case for accommodating the gas sensor and the third filter.

The accommodation case may include: a first surface at least partially opened to communicate with the gas tank and the hole, and attached in parallel to at least one among the first connecting hose to the third connecting hose; a second surface disposed in parallel to at least one among the first connecting hose to the third connecting hose, and facing the first surface; a third surface perpendicular to at least one among the first connecting hose to the third connecting hose, and connecting the first surface and the second surface; and a fourth surface facing the third surface, perpendicular to at least one among the first connecting hose to the third connecting hose, and connecting the first surface and the second surface.

The third filter may be installed to be spaced apart from the first surface by a predetermined distance, and a first side surface may be attached to the third surface of the accommodation case, and a second side surface facing the first side surface is attached to the fourth surface of the accommodation case to remove moisture from the gas that has passed through the gas tank and the hole and transfer the gas to the gas sensor.

The gas sensor may be installed on the second surface of the accommodation case.

The automatic urine treatment system may further include a gas sensor unit, and at least one among the first connecting hose to the third connecting hose may include a gas inlet connecting hose through which gas flows in and a gas discharge connecting hose through which gas is discharged. The gas inlet connecting hose and the gas discharge connecting hose may communicate with the accommodation case, and the accommodation case may be embedded with a gas sensor for sensing gas of the excrement and a third filter for filtering moisture flowing into the gas sensor.

BRIEF DESCRIPTION OF THE DRAWINGS

FIG. 6 is a view showing a gas sensor unit installed in a connecting hose according to a second embodiment of the present invention.

DETAILED DESCRIPTION OF THE PREFERRED EMBODIMENT

Figure 1:
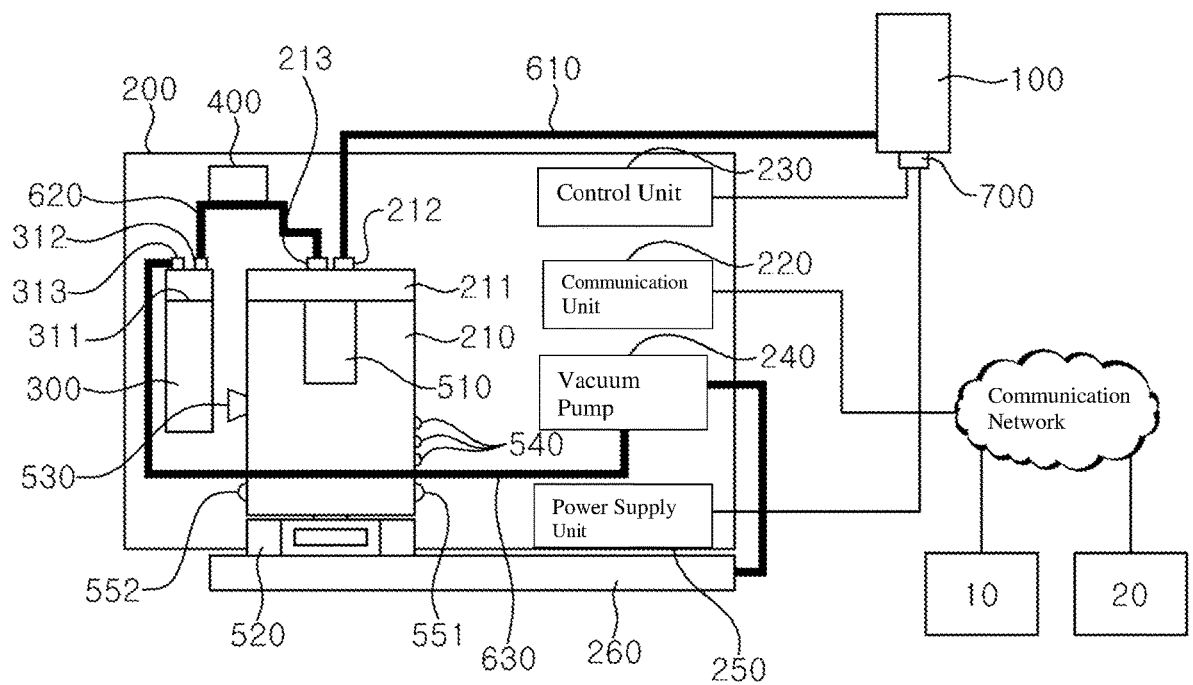
FIG. 1 is a block diagram showing a urine treatment system according to an embodiment of the present invention.
Figure 2:
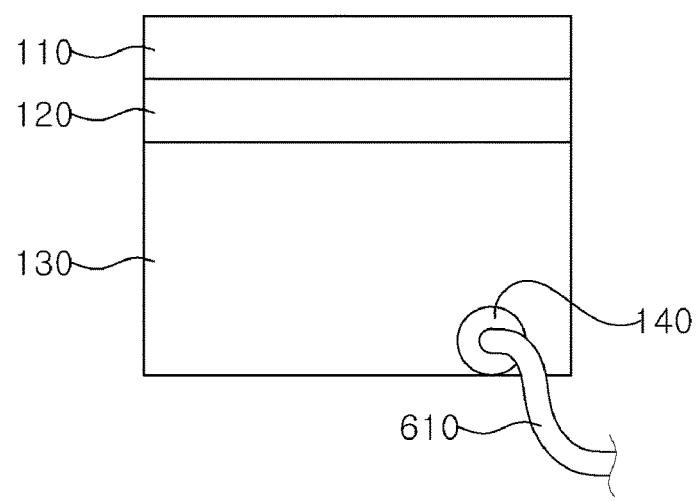
FIG. 2 is a view showing a receiver according to an embodiment of the present invention.

An automatic urine treatment system according to an embodiment of the present invention includes a receiver 100, a main body 200, and a first connecting hose 610 to a third connecting hose 630.

<Receiver (100)>

The receiver 100 of the present invention contacts wearer's buttocks and receives wearer's excrement. The receiver 100 includes a first filter unit 110, a urine storage unit 130, and a urine detection sensor 120.

1. First Filter Unit (110)

The first filter unit 110 is disposed at a portion contacting the wearer's skin, filters solid components from the excrement, and transfers the excrement from which the solid components are removed to the urine storage unit 130.

The first filter unit 110 includes a first filter body made of a fiber of a water-permeable material formed with a mesh or pores.

In addition, the first filter unit 110 may contain a plant-derived extract in the fiber of a water-permeable material to prevent skin disease of the wearer and remove odor of the excrement. The plant-derived extract has an advantage of not causing skin trouble unlike chemical components, while removing bacteria contained in the excrement and the odor.

The plant-derived extract may contain at least one among grapefruit seed extract, kiwi fruit extract, camellia extract, chamomile extract, lavender extract, rosemary extract, coconut extract, and olive extract.

The grapefruit seed extract exhibits very excellent antibacterial activity against gram-negative bacteria, gram-positive bacteria, and true fungi including fungi and yeast.

The camellia tree extract has inflammation suppressing and inflammation killing functions and may prevent skin trouble of a wearer.

The kiwi fruit extract has a strong antifungal effect against Candida bacteria that cause vaginitis of women and thus may prevent vaginitis of a female wearer.

The camellia extract has inflammation suppressing and inflammation killing effects and may prevent skin trouble of a wearer.

The chamomile extract has a high antibacterial activity effect and may remove bacteria contained in the excrement.

The lavender extract and the rosemary extract have high antibacterial activity against gram-negative bacteria.

The coconut extract and the olive extract may increase antibacterial activity and form a protective film on the skin to prevent skin trouble of a wearer.

The total amount of the plant extract may be 1 to 10 parts by weight when the weight of the first filter body is 100.

In addition, the plant extract may contain 1 to 5 parts by weight of grapefruit seed extract, 1 to 2 parts by weight of kiwi fruit extract, 0.5 to 2 parts by weight of camellia extract, 1 to 3 parts by weight of chamomile extract, 1 to 3 parts by weight of lavender extract, 1 to 3 parts by weight of rosemary extract, 1 to 2 parts by weight coconut extract, and 1 to 2 parts by weight of olive extract.

Alternatively, the first filter unit 110 may include nano zinc polypeptide in the first filter body. The zinc polypeptide has an immediate and lasting antibacterial deodorant effect while being harmless to human bodies. In addition, even with a small amount of use, a sterilizing effect of converging the survival rate of gram-positive bacteria and gram-negative bacteria to zero is obtained, and more than 99.8% of various stink and odor components can be removed.

2. Urine Storage Unit (130)

The urine storage unit 130 is disposed under the first filter unit 110. As described above, the urine storage unit 130 may receive and store liquid, i.e., the excrement from which at least some of the solid component has been removed by filtering the solid component, from the first filter unit 110.

The urine storage unit 130 may be made of a fiber of a highly water-permeable material in the form of an absorption layer that absorbs and stores the excrement of liquid component.

Alternatively, the urine storage unit 130 may be configured as a non-water permeability soft container having an open top surface to store the excrement of liquid component inside the container.

Alternatively, the urine storage unit 130 may be configured in the form of a urinal-cup to store the excrement of liquid component in the cup.

The urine storage unit 130 may include a urine drainage hole 140 through which the first connecting hose 610 passes. The urine drainage hole 140 may be connected to the first connecting hose 610 to transfer the stored excrement of liquid component toward the urine tank 210.

3. Urine Detection Sensor (120)

The urine detection sensor 120 may be disposed between the first filter unit 110 and the urine storage unit 130.

The urine detection sensor 120 is for detecting urine of a wearer, and may detect urine using a sensing method of detecting urine by sensing a change in impedance between electrodes, a sensing method of detecting urine by sensing a change in temperature, and a sensing method of detecting urine by sensing a chemical change.

The urine detection sensor 120 generates a urine detection signal when urine is detected. The urine detection signal is directly transferred from the urine detection sensor 120 to the control unit 230 described below, or transferred from the urine detection sensor 120 to the terminal 700 described below.

<Connecting Hose>

According to an embodiment of the present invention, the connecting hose may include a first connecting hose 610 of which one end is connected to the urine drainage hole 140 and the other end is connected to the urine tank 210, a second connecting hose 620 of which one end is connected to the urine tank 210 and the other end is connected to an auxiliary tank 300, and a third connecting hose 630 of which one end is connected to the auxiliary tank 300 and the other end is connected to the vacuum pump 240.

The first connecting hose 610 has a channel formed therein to move urine and gas stored in the urine storage unit 130 to the urine tank 210.

A wire passage channel through which a sensor wire connecting the urine detection sensor 120 and the control unit 230 described below passes may be formed outside the first connecting hose 610.

Alternatively, the wire passage channel may be formed separately from the first connecting hose 610 and connected to the urine detection sensor 120 and the control unit 230 described below.

Alternatively, the wire passage channel may be formed separately from the first connecting hose 610 and connected to the terminal 700 described below and the control unit 230 described below.

A gas tank and a hole through which gas contained in excrement may pass may be formed on one side of at least one among the first connecting hose 610 to the third connecting hose 630. In addition, a gas sensor unit 400 for sensing the gas component contained in the excrement is formed on one side of at least one among the first connecting hose 610 to the third connecting hose 630 where the gas tank and the hole are formed.

As described below, according to an embodiment of the present invention, water vapor among the gas component flowing into the auxiliary tank 300 through the second connecting hose 620 flows in and is stored in the auxiliary tank 300. Therefore, the gas sensor unit 400 is preferably installed on one side of the second connecting hose 620.

Hereinafter, although it is configured to install the gas sensor unit 400 in the second connecting hose 620 for convenience, the scope of the present invention is not limited thereto, and it may also be installed in the first connecting hose 610 or the third connecting hose 630 according to the situation.

First Embodiment of Gas Sensor Unit (400)

Figure 5:
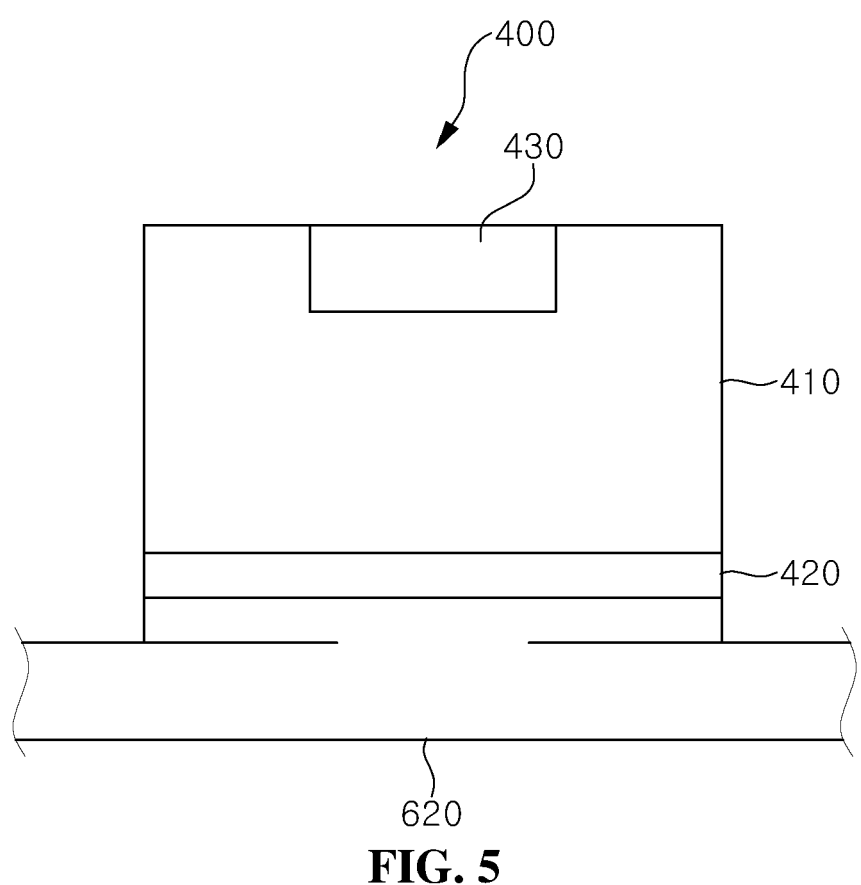
FIG. 5 is a view showing a gas sensor unit installed in a connecting hose according to a first embodiment of the present invention.

Referring to FIG. 5, a gas sensor unit 400 according to a first embodiment of the present invention may include an accommodation case 410, a third filter 420, and a gas sensor 430.

The accommodation case 410 accommodates the third filter 420 and the gas sensor 430. The accommodation case 410 may include a first surface at least partially opened to communicate with the gas tank and the hole, and attached in parallel to the second connecting hose 620, a second surface disposed in parallel to the second connecting hose 620, and facing the first surface, a third surface perpendicular to the second connecting hose 620, and connecting the first surface and the second surface, and a fourth surface facing the third surface, perpendicular to the second connecting hose 620, and connecting the first surface and the second surface.

The third filter 420 is installed to be spaced apart from the first surface of the accommodation case 410 by a predetermined distance. A first side surface of the third filter 420 is attached to the third surface of the accommodation case 410, and a second side surface of the third filter 420 facing the first side surface is attached to the fourth surface of the accommodation case 410. The third filter 420 removes moisture from the gas that has passed through the gas tank and the hole, and transfers the gas to the gas sensor 430.

The gas sensor 430 is installed on the second surface of the accommodation case 410, and a gas sensing signal sensed by the gas sensor 430 is transferred to the control unit 230 through wired or wireless communication.

Since the gas sensor 430 is mounted outside the receiver 100 and the second connecting hose 620 and embedded in the separate accommodation case 410, a large amount of gas may not flow into the gas sensor 430, and corrosion of the gas sensor 430 by the excrement gas may be prevented.

In addition, since the gas component from which moisture is removed by the third filter 420 flows into the gas sensor 430, there is an advantage of preventing corrosion of the gas sensor 430 caused by the moisture, and enhancing sensing accuracy and extending the lifespan of the gas sensor 430.

Second Embodiment of Gas Sensor Unit (400)

Referring to FIG. 6, a gas sensor unit 400 according to a second embodiment of the present invention may include an accommodation case 411, a third filter 420, and a gas sensor 430. In addition, the second connecting hose 620 includes a gas inlet connecting hose 621 for transferring gas to the accommodation case, and a gas discharge connecting hose 622 for receiving gas discharged from the accommodation case 411.

The accommodation case 411 may include a first communication hole 441 communicating with the gas inlet connecting hose 621 and a second communication hole 442 communicating with the gas discharge connecting hose 622.

The air inside the urine tank 210 is transferred inside the accommodation case 411 through the gas inlet connecting hose 621 and the first communication hole 441 in order.

The air transferred into the accommodation case 411 reaches the third filter 420 and is transferred to the gas sensor 430 after moisture is removed.

The third filter 420 and the gas sensor 430 may be installed to be attached to a first surface and a second surface perpendicular to the gas inlet connecting hose 621.

Like the first embodiment, the gas sensor 430 transfers the sensed gas sensing signal to the control unit 230 through wired or wireless communication.

<Main Body (200)>

The main body 200 according to an embodiment of the present invention may include a urine tank 210 for storing urine, a vacuum pump 240, a second filter unit 260, a control unit 230, a communication unit 220, and an auxiliary tank 300.

The urine tank 210, the vacuum pump 240, the control unit 230, the communication unit 220, and the auxiliary tank 300 are accommodated inside the main body 200. The second filter unit 260 may be accommodated under the urine tank 210 or may be mounted on an outer bottom surface of the main body 200.

1. Urine Tank (210)

The urine tank 210 is formed to have an open top surface and may be provided with a urine tank cover 211 that covers and seals the opened portion of the urine tank 210. A first urine suction unit 212 and a first gas transfer unit 213 are formed on the top surface of the urine tank cover 211.

The first urine suction unit 212 is connected to the first connecting hose 610, and the first gas transfer unit 213 is connected to the second connecting hose 620.

The urine tank 210 transfers negative pressure to the urine storage unit 130 and receives urine and gas from the urine storage unit 130 through the first urine suction unit 212 connected to the first connecting hose 610.

The urine tank 210 receives negative pressure from the auxiliary tank 300 and transfers gas contained in excrement toward the auxiliary tank 300 through the first gas transfer unit 213.

A float sensor 510 for detecting the level of the urine stored in the urine tank 210, generating a urine level signal indicating the level of the stored urine, and transferring the generated urine level signal to the control unit 230 may be installed on one side of the urine tank cover 211.

A mass sensor 520 for detecting the mass of the urine stored in the urine tank 210, generating a urine mass signal indicating the detected mass of the urine, and transferring the generated urine mass signal to the control unit 230 may be installed on the outer surface of the urine tank 210. Preferably, the mass sensor 520 may be installed under the bottom surface of the urine tank 210.

A foam detection sensor 530 installed on the outer surface of the urine tank 210 to detect foam of the urine and generate a foam detection signal when the foam of the urine reaches a preset range may be included on the outer surface of the urine tank 210. The foam detection sensor 530 may be an infrared sensor.

At least one among the urine level signal generated by the float sensor 510, the urine mass signal generated by the mass sensor 520, and the foam detection signal generated by the foam detection sensor 530 may be transferred to the control unit 230 through wired or wireless communication.

When the received urine level value is out of a preset range, the received urine mass information is out of a preset range, or the foam detection signal is received, the control unit 230 may generate and transfer a driving stop control signal to the vacuum pump 240 to stop driving of the vacuum pump 240.

When the driving stop control signal is received, the vacuum pump 240 may stop driving to prevent flow of the urine into the urine tank 210.

According to an embodiment of the present invention, a strip 800 capable of monitoring the wearer's health condition through urine may be mounted inside the urine tank 210.

In the strip 800, pads 820 containing a detection reagent may be attached to a strip support 810 made of a plastic or paper material. The pad 820 containing the detection reagent is referred to as a color change unit 820 in the present invention. The strip 800 may include a plurality of color change units 820 changing color when urine touches in order to analyze various components in the urine at once. Preferably, the color change unit 820 changes to another color according to a predetermined reaction table according to the presence or amount of urobilinogen, glucose, ketone, bilirubin, protein, nitrite, pH, blood, specific gravity, and white blood cells contained in the urine.

According to a first embodiment of the present invention, the strip 800 may be mounted on the strip mounting unit 900.

The strip mounting unit 900 may include a first support unit 910 for supporting the strip support 810 in the longitudinal direction, a second support unit 930 perpendicular to the first support unit 910 and supporting a first surface of the strip support 810, and a latch unit 920 for supporting a second surface of the strip support 630 and latching the strip mounting unit 900 on one side of the urine tank 210.

Figure 4:
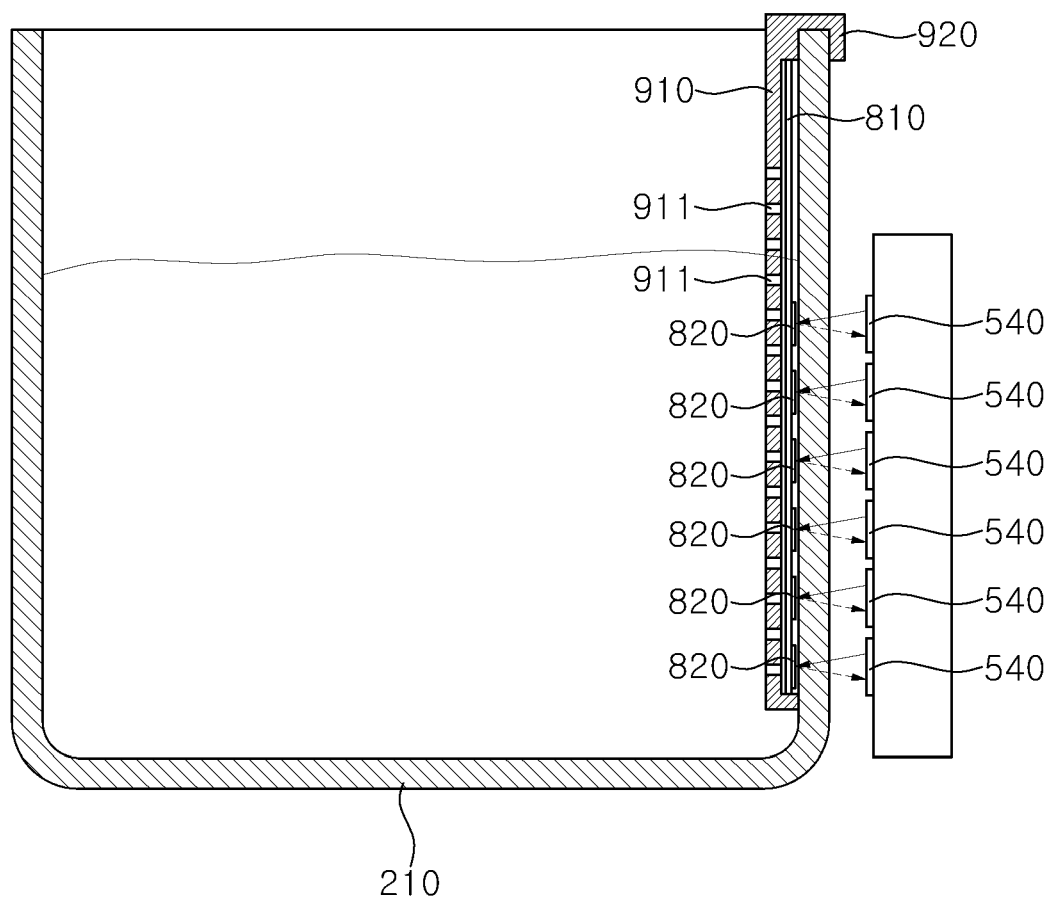
FIG. 4 is a view showing a urine tank equipped with a strip mounting unit according to an embodiment of the present invention.

Although FIG. 4 shows that the strip mounting unit 900 is mounted on the top surface of the urine tank 210 for convenience, the strip mounting unit 900 may be mounted on the side surface or the bottom surface of the urine tank 210 depending on circumstances.

The first support unit 910 has a plurality of openings 911 through which the urine stored in the urine tank 210 may flow. The urine stored in the urine tank 210 may be transferred to the color change units 820 through the openings 911.

Figure 3:
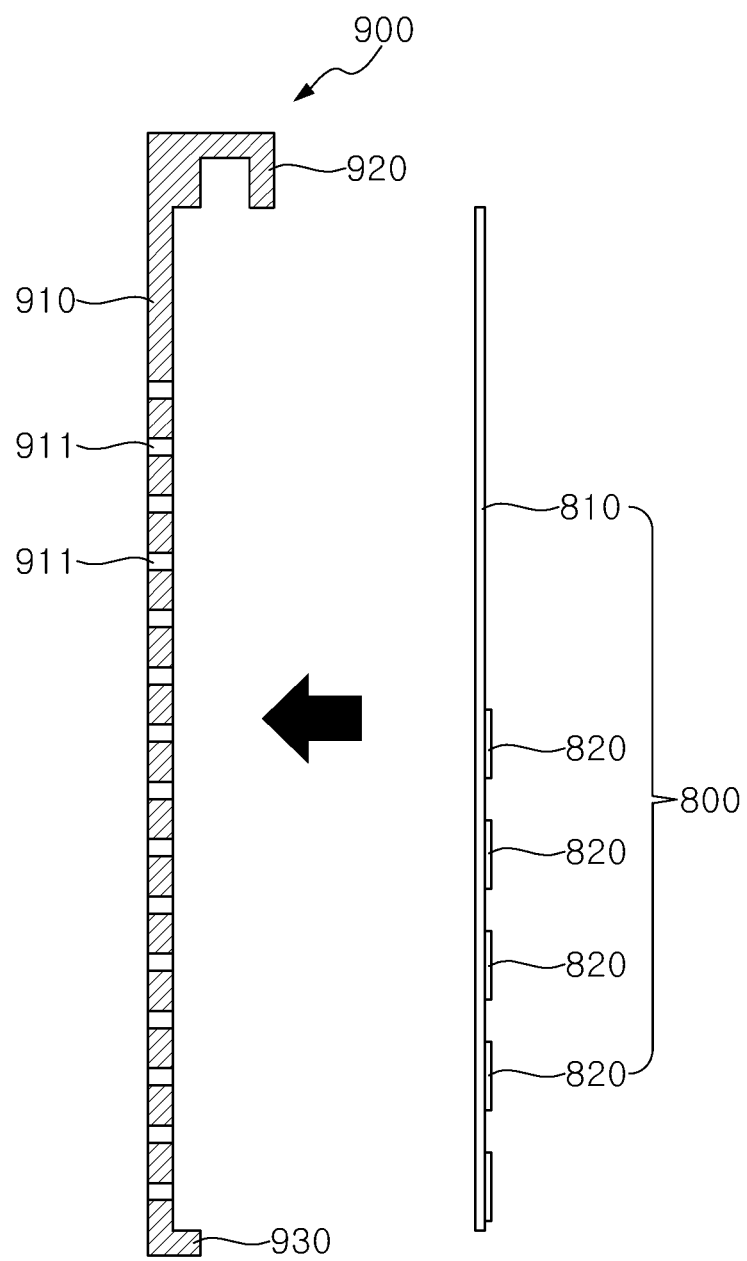
FIG. 3 is a view showing a strip and a strip mounting unit according to an embodiment of the present invention.

Referring to FIG. 3, the first support unit 910 and the second support unit 930 are formed to be perpendicular to each other, so that the first support unit 910 may support the strip support 810 of the longitudinal direction, and the second support unit 930 may support the strip support 810 of a direction perpendicular to the longitudinal direction. Preferably, a second surface (the bottom surface in the drawing) of the first support unit 910 may be bent vertically to form the second support unit 930.

The latch unit 920 is formed to be perpendicular to the first support unit 910 to face the second support unit 930. The latch unit 920 may be formed to be perpendicular to the first support unit 910 on a first surface of the first support unit 910. The first and second surfaces of the first support unit 910 face each other.

The length of the outer surface of the latch unit 920 is formed to be longer than the length of the inner surface as much as the horizontal length of the first support unit 910.

The latch unit 920 includes a cutout unit that is cut in a rectangular shape having a horizontal surface of a first length and a vertical surface of a second length. The first length is smaller than the length of the horizontal surface of the latch unit 920, and the second length is smaller than the length of the vertical surface of the latch unit 920.

The inner surface of the latch unit 920 has a shape bent twice through the cutout unit. A first bent unit bent first is extended from the inner surface of the first support unit 910 in a direction perpendicular to the first support unit 910 as much as a third length, bent in a direction parallel to the first support portion 910, and extended as much as a second length. Then, the bent second bent unit is connected to the end of the first bent unit extended as much as the second length, extended starting from a direction perpendicular to the first support unit 910 as much as the first length, bent in a direction parallel to the first support unit 910, and then extended as much as the second length. Referring to FIG. 3, the first bent unit is bent in a '⌐' shape, and the second bent unit is bent in a '⌐' shape.

One side of the strip support 810 is seated in and supported by the first bent unit, and the second bent unit, which is a second bent portion, is seated on one surface of the urine tank 210. Referring to FIG. 3, the vertical portion of the first bent unit and the horizontal portion of the second bent unit are connected to each other.

As the components of the urine stored in the urine tank 210 are detected by opening the urine tank cover 211 and latching the strip mounting unit 900 on one side of the urine tank 210, there is an advantage in that the sealing force of the urine tank 210 is not weakened. In addition, it is also advantageous in that cleaning is easy when the urine tank 210 is cleaned since only the strip mounting unit 900 needs to be removed.

As one side surface of the urine tank 210 on which the strip mounting unit 900 is mounted is formed of a transparent material, color change of the color change units 820 may be easily detected with naked eyes. In addition, at least one first optical sensor unit 540 may be disposed on the outer surface of the urine tank 210 in order to automatically detect color change of the strip 800.

As many first optical sensor units 540 as the number of the color change units 820 are installed at the locations corresponding to the positions of the color change units 820. Preferably, the first optical sensor units 540 may be detachably installed at the locations corresponding to the positions of the color change units 820.

When the strip 800 includes six color change units 820 capable of detecting urobilinogen, glucose, ketone, bilirubin, protein, and nitrite contained in the urine, a total of six first optical sensor units 540 may be installed at the locations corresponding to the positions of the six color change units 820, respectively.

Alternatively, the first optical sensor unit 540 may include a single light source, a transmission unit for distributing light emitted from the single light source and outputting the light to each color change unit 820, and a plurality of light receiving units for receiving light reflected from each color change unit 820.

Information on the strip color change sensed by the first optical sensor unit 540 may be transferred to the control unit 230.

A second optical sensor unit for sensing at least one among turbidity and color change of the urine stored in the urine tank 210 may be included on the side surface of the urine tank 210. A light receiving unit 552 of the second optical sensor unit is installed on a first outer surface of the urine tank 210, and a light emitting unit 551 of the second optical sensor unit is installed on a second outer surface of the urine tank 210 to sense least one among the turbidity and the color change of the urine stored in the tank 210 and transfer urine turbidity information and urine color information to the control unit 230.

2. Auxiliary Tank (300)

The auxiliary tank 300 is formed to have an open top surface and may be provided with a second urine tank cover 311 that covers and seals the opened portion of the auxiliary tank 300. A second gas transfer unit 312 and a third gas transfer unit 313 are formed on the top surface of the second urine tank cover 311.

The second gas transfer unit 312 is connected to the second connecting hose 620, and the third gas transfer unit 313 is connected to the third connecting hose 630.

The auxiliary tank 300 transfers negative pressure to the urine tank 210 through the second gas transfer unit 312 connected to the second connecting hose 620, and receives gas contained in the excrement from the urine tank 210.

The auxiliary tank 300 receives the negative pressure from the vacuum pump 240 through the third gas transfer unit 313 and transfers the gas contained in the excrement toward the vacuum pump 240.

The auxiliary tank 300 receives the gas contained in the excrement from the urine tank 210. This gas also includes water vapor vaporized from water. The auxiliary tank 300 may prevent transfer of moisture to the vacuum pump 240 by condensing and storing the received water vapor.

The capacity of the auxiliary tank 300 may be 0.1 to 0.5 when the capacity of the urine tank 210 is set to 1.

3. Vacuum Pump (240)

The vacuum pump 240 of the present invention is connected to the control unit 230 and operates according to a control signal generated by the control unit 230.

The urine sensor 120 may generate and transmit a urine detection signal to the terminal 700 mounted on the receiver 100 through wired or wireless communication. The terminal 700 may transfer the received urine detection signal to the control unit 230 through wireless or wired communication. When the urine detection signal is received, the control unit 230 may generate and transfer a driving start signal for driving the vacuum pump 240 to the vacuum pump 240.

The vacuum pump 240 operates when the driving start signal is received from the control unit 230. When the vacuum pump 240 operates, a negative pressure is formed by sucking the air in the urine tank 210. The negative pressure formed in this way is transferred to the auxiliary tank 300 through the third connecting hose 630. The negative pressure applied to the auxiliary tank 300 is transferred to the urine tank 210 through the second connecting hose 620. The negative pressure applied to the urine tank 210 is transferred to the urine drainage hole 140 of the receiver 100 through the first connecting hose 610. The negative pressure is transferred to the urine storage unit 130 of the receiver 100 through the urine drainage hole 140, and as the negative pressure is applied to the urine storage unit 130, the urine and the gas stored in the urine storage unit 130 are transferred to the urine tank 210 through the urine drainage hole 140 via the first connecting hose 610.

In addition, the vacuum pump 240 may blow the gas transferred through the third connecting hose 630 toward the second filter unit 260.

4. Control Unit (230)

The control unit 230 may receive a urine detection signal from the terminal 700 or directly receive the urine detection signal from the urine detection sensor 110 through wired or wireless communication. When the urine detection signal is received, the control unit 230 generates and transfers a driving start signal that controls to drive the vacuum pump 240 to the vacuum pump 240. When the driving start signal is received, the vacuum pump 240 is driven and generates a negative pressure.

In addition, the control unit 230 may receive a urine level signal from the float sensor 510 through wired or wireless communication, a urine mass signal from the mass sensor 520 through wired or wireless communication, and a foam detection signal from the foam detection sensor 530 through wired or wireless communication.

The control unit 230 may generate a first danger signal when the urine level is greater than or equal to a preset range based on the received urine level signal. In addition, the control unit 230 may generate a second danger signal when the mass of the urine is greater than or equal to a preset range based on the received urine mass signal. In addition, the control unit 230 may generate a third danger signal when a foam detection signal is received from the foam detection sensor 530.

In addition, the control unit 230 may generate and transfer a driving stop control signal for controlling to stop driving of the vacuum pump 240 to the vacuum pump 240 when at least one among the first to third danger signals is generated. The vacuum pump 240 may stop driving to prevent flow of moisture into the vacuum pump 240 when the driving stop control signal is received.

In addition, the control unit 230 may receive gas sensing information from the gas sensor 430 and distinguish between feces and fart. The control unit 230 forms a graph using the horizontal axis as the time axis and the vertical axis as the gas level axis based on the gas sensing information, and when the peak of the gas level lasts for a predetermined time, it is determined as feces, and when it does not last for the predetermined time, it is determined as fart.

When feces is detected based on the gas sensing information, the control unit 230 transfers a signal for replacing the receiver 100 to the communication unit 220, and when the signal for replacing the receiver 100 is received, the communication unit 220 transfers the signal to the terminal 10 or 20 of the guardian or medical staff to replace the receiver 100.

The control unit 230 may receive strip color change information from the first optical sensor unit 540 through wired or wireless communication, and urine turbidity information and urine color information from the second optical sensor unit.

The control unit 230 previously stores strip color change information according to health conditions, and compares the received strip color change information with the previously stored strip color change information. The strip color change information stored in the control unit 230 may include first strip color change information indicating a healthy state, second strip color change information indicating an abnormal health state, and a third strip color indicating a serious problem in the health state.

When the received strip color change information matches the second strip color change information, the control unit 230 may generate a first health state abnormal signal indicating an abnormal health state, and transfers the first health state abnormal signal and the received strip color change information to the communication unit 220.

In addition, when the received strip color change information matches the third strip color change information, the control unit 230 may generate a second health state abnormal signal indicating a serious problem in the health state, and transfers the second health state abnormal signal and the received strip color change information to the communication unit 220.

In addition, when the second health state abnormal signal is generated, the control unit 230 may generate a first alarm device driving signal to trigger a visual or audible alarm through an alarm device (not shown) installed outside the main body 200, and immediately inform that there is a serious problem in the health state of the wearer. When the alarm is generated in this way, the medical staff may directly see the color change of the strip 800 with naked eyes and detect early that the patient is in a dangerous condition.

In addition, the control unit 230 stores urine turbidity information and urine color information according to the health conditions, and compares urine turbidity information and urine color information received from the second sensor unit through wired or wireless communication with the previously stored urine turbidity information and urine color information. The urine turbidity information and urine color information stored in the control unit 230 may include first urine information indicating a healthy state, second urine information indicating an abnormal health state, and third urine information indicating that there is a serious problem in the health state.

When the received urine turbidity information and urine color information match the second urine information, a third health state abnormal signal indicating an abnormal health state is generated. The control unit may transfer the generated third health state abnormal signal and the received urine turbidity information and urine color information to the communication unit 220.

In addition, when the received urine turbidity information and urine color information match the third urine information, the control unit 230 may generate a fourth health state abnormal signal indicating that there is a serious problem in the health state, and transfer the fourth health state abnormal signal and the received urine turbidity information and urine color information to the communication unit 220.

In addition, when the fourth health state abnormal signal is generated, the control unit 230 may generate a second alarm device driving signal to trigger a visual or audible alarm through an alarm device (not shown) installed outside the main body 200, and immediately inform that there is a serious problem in the health state of the wearer. When the alarm is generated in this way, the medical staff may directly see the stored urine turbidity and urine color with naked eyes and detect early that the patient is in a dangerous condition.

In addition to those described above, the control unit 230 of the present invention may supply dry air to the receiver 100 or generate a control signal for driving the vacuum pump 240 depending on operating conditions according to various environments, such as transferring air to the second filter unit 260 described below.

5. Communication Unit (220)

In addition, the communication unit 220 may transfer the first health state abnormal signal and the strip color change information from the control unit 230 to the guardian terminal 10 or the medical staff terminal 20.

In addition, the communication unit 220 may transfer the second health state abnormal signal and the strip color change information from the control unit 230 to the guardian terminal 10 or the medical staff terminal 20.

In addition, the communication unit 220 may transfer the third health state abnormal signal, the urine turbidity information, and the urine color information from the control unit 230 to the guardian terminal 10 or the medical staff terminal 20.

In addition, the communication unit 220 may transfer the fourth health state abnormal signal, the urine turbidity information, and the urine color information from the control unit 230 to the guardian terminal 10 or the medical staff terminal 20.

6. Power Supply Unit (250)

The power supply unit 250 according to an embodiment of the present invention may supply power to the vacuum pump 240, the communication unit 220, and the control unit 230. In addition, the power supply unit 250 may be connected to the terminal 700 through a wire and supply power to the terminal 700. The terminal 700 connected to the conventional receiver 100 is embedded with a battery. However, the terminal 700 embedded with a battery as described above has a disadvantage in that the vacuum pump 240 is not driven since the urine detection signal transmitted from the receiver 100 is not received when the battery is exhausted. In particular, in the case where the vacuum pump 240 does not operate properly during the late night when the healthcare assistants are absent for a long time, urine of the receiver 100 is not discharged, and this causes skin erosion of the wearer and indoor air pollution.

7. Second Filter Unit (260)

The second filter unit 260 according to an embodiment of the present invention may receive the air flowing out from the urine tank 210, filter the air, and discharge the air to the outside of the automatic urine treatment system.

Although the air is sterilized through a UV lamp conventionally, skin rash or erythema occurs when the skin is excessively exposed to the UV lamp, and it is known that skin cancer is caused when the skin is overexposed.

To solve this problem, in the present invention, the second filter unit 260 may be formed by mixing natural plant-derived powder with activated carbon having an excellent odor removal function, and hardening the mixture.

The second filter unit 260 is generated through the process described below.

The second filter unit 260 may be manufactured in the steps of crushing activated carbon, obtaining eucalyptus powder by vacuum-drying and crushing eucalyptus extract extracted using ethanol, obtaining lotus leaf powder by vacuum-drying and crushing lotus leaf extract extracted using ethanol, and forming a block by uniformly mixing the activated carbon crushed powder, the eucalyptus powder, the lotus leaf powder, and a resin binder and molding the mixture.

Activated carbon is known to be the most excellent one in removing odor among natural substances. Eucalyptus terpenes oxidize in the air and generate ozone, and the ozone generated in this way has a strong sterilizing effect. Lotus leaves have excellent deodorizing and antibacterial effects.

The solid block manufactured by mixing the activated carbon, the eucalyptus, and the lotus leaves is a natural plant-derived material harmless to the human body, while having excellent deodorizing, antibacterial, and sterilizing effects.

Alternatively, the second filter unit 260 may be manufactured in the steps of crushing activated carbon, obtaining eucalyptus powder by vacuum-drying and crushing eucalyptus extract extracted using ethanol, obtaining lotus leaf powder by vacuum-drying and crushing lotus leaf extract extracted using ethanol, obtaining chlorine dioxide powder, and forming a block by uniformly mixing the activated carbon crushed powder, the eucalyptus powder, the lotus leaf powder, the chlorine dioxide powder, and a resin binder and molding the mixture.

The present invention has an advantage of preventing failure of the vacuum tank by removing moisture transferred to the vacuum pump through the auxiliary tank.

The present invention has an advantage of caring health of elderly or disabled people by mounting a strip for analyzing components of urine through a color change in the urine tank, analyzing the color change through a first optical sensor, and transferring a result thereof to the terminal of a guardian or a medical staff.

In addition, the present invention has an advantage of preventing skin trouble of a wearer by including a substance having antibacterial, sterilizing, and deodorizing functions of natural plant-derived components in the first filter unit of the receiver contacting the wearer's skin.

In addition, the present invention has an advantage of purifying the air of a room in which the urine tank is installed by including the second filter unit that removes germs or odor contained in the excrement flowing out from the urine tank.

The invention claimed is:

1. An automatic urine treatment system comprising:
a receiver for receiving a wearer's excrement;
a main body including a urine tank for receiving and storing urine from the receiver, and a vacuum pump for sucking air into the urine tank and transferring a negative pressure to the receiver;
a first connecting hose connecting the receiver and the urine tank;
an auxiliary tank connected to the urine tank and the vacuum pump;
a second connecting hose of which one end is connected to the urine tank and the other end is connected to the auxiliary tank; and
a third connecting hose of which one end is connected to the auxiliary tank and the other end is connected to the vacuum pump, wherein:
a strip for analyzing components of the stored urine through color change is mounted inside the urine tank,
the urine tank further includes a first optical sensor unit for sensing the color change of the strip, and a second optical sensor unit for sensing at least one of turbidity and a urine color of the stored urine, a gas tank and a hole through which gas contained in excrement may pass are formed on one side of at least one among the first connecting hose to the third connecting hose, a gas sensor unit includes a gas sensor for sensing a gas component of the excrement, a third filter for removing moisture of the gas, and an accommodation case for accommodating the gas sensor and the third filter, the accommodation case includes a first surface at least partially opened to communicate with the gas tank and the hole, and attached in parallel to at least one among the first connecting hose to the third connecting hose, a second surface disposed in parallel at least one among the first connecting hose to the third connecting hose, and facing the first surface, a third surface perpendicular to at least one among the first connecting hose to the third connecting hose, and connecting the first surface and the second surface, and a fourth surface facing the third surface, perpendicular to at least one among the first connecting hose to the third connecting hose, and connecting the first surface and the second surface, the third filter is installed to be spaced apart from the first surface by a predetermined distance, a first side surface is attached to the third surface of the accommodation case, and a second side surface facing the first side surface is attached to the fourth surface of the accommodation case to remove moisture from the gas that has passed through the gas tank and the hole and transfer the gas to the gas sensor, and the gas sensor is installed on the second surface of the accommodation case.

2. The system according to claim 1, wherein the strip includes a plurality of color change units for analyzing the components contained in the urine, wherein as the first optical sensor unit is installed in plurality at positions corresponding to the plurality of color change units, or light emitted from a single light source is split into as many lights corresponding to the color change units and transferred to each of the color change units, the first optical sensor units detect color change of the plurality of color change units.

3. The system according to claim 1, wherein the urine tank includes:
a float sensor installed inside the urine tank to detect a level of the urine stored in the urine tank, and generate a urine level signal indicating the level of the stored urine;
a mass sensor installed on an outer surface of the urine tank to detect a mass of the urine stored in the urine tank, and generate a urine mass signal indicating the mass of the stored urine; and
an infrared sensor installed on the outer surface of the urine tank to detect foam of the urine, and generate a foam detection signal when the foam of the urine reaches a preset range.

4. The system according to claim 1, wherein the strip includes a strip support attached with a color change unit that changes color according to the urine components, and the strip support is mounted on a strip mounting unit, and the strip mounting unit accommodates the strip support and is mounted on one side of the urine tank.

5. The system according to claim 4, wherein the strip mounting unit includes:
a first support unit for supporting the strip support in a longitudinal direction;
a second support unit perpendicular to the first support unit and supporting a first surface of the strip support; and
a latch unit for supporting a second surface of the strip support and mounting the strip mounting unit on one side of the urine tank.

6. The system according to claim 5, wherein the latch unit includes a first bent unit and a second bent unit connected to the first bent unit, wherein
the first bent unit supports the second surface of the strip support, and the second bent unit is mounted on one side of the urine tank.

7. The system according to claim 1, wherein the receiver includes a first filter unit for filtering at least some of solid components from the excrement, wherein
the first filter unit includes a first filter body having a mesh or pore structure of a water-permeable material, and at least one among grapefruit seed extract, kiwi fruit extract, camellia extract, chamomile extract, lavender extract, rosemary extract, coconut extract, olive extract, and zinc polypeptide is contained in the first filter body.

8. The system according to claim 1, further comprising a second filter unit, wherein
the second filter unit is manufactured as a solid block by mixing and molding eucalyptus extract powder, lotus leaf extract powder, and a binder with activated carbon, or manufactured as a solid block by mixing and molding eucalyptus extract powder, lotus leaf extract powder, chlorine dioxide powder, and a binder with activated carbon.

9. An automatic urine treatment system comprising:
a receiver for receiving a wearer's excrement;
a main body including a urine tank for receiving and storing urine from the receiver, and a vacuum pump for sucking air into the urine tank and transferring a negative pressure to the receiver;
a first connecting hose connecting the receiver and the urine tank;
an auxiliary tank connected to the urine tank and the vacuum pump;
a second connecting hose of which one end is connected to the urine tank and the other end is connected to the auxiliary tank;
a third connecting hose of which one end is connected to the auxiliary tank and the other end is connected to the vacuum pump;
a gas sensor unit; and
an accommodation case embedded with a gas sensor for sensing gas of the excrement and a third filter for filtering moisture flowing into the gas sensor, wherein:
a strip for analyzing components of the stored urine through color change is mounted inside the urine tank,
the urine tank further includes a first optical sensor unit for sensing the color change of the strip, and a second optical sensor unit for sensing at least one of turbidity and a urine color of the stored urine,
at least one among the first connecting hose to the third connecting hose includes a gas inlet connecting hose through which gas flows in and a gas discharge connecting hose through which gas is discharged, and
the gas inlet connecting hose and the gas discharge connecting hose communicate with the accommodation case.

* * * * *